(12) United States Patent
Miyamoto et al.

(10) Patent No.: US 10,106,685 B2
(45) Date of Patent: Oct. 23, 2018

(54) COLORED METALLIC PIGMENT

(71) Applicant: TOYO ALUMINIUM KABUSHIKI KAISHA, Osaka-shi, Osaka (JP)

(72) Inventors: Kenichi Miyamoto, Osaka (JP); Takayuki Nakao, Osaka (JP); Taro Morimitsu, Osaka (JP)

(73) Assignee: TOYO ALUMINIUM KABUSHIKI KAISHA, Osaka-Shi (JP)

( * ) Notice: Subject to any disclaimer, the term of this patent is extended or adjusted under 35 U.S.C. 154(b) by 0 days.

(21) Appl. No.: 15/508,004

(22) PCT Filed: Jul. 2, 2015

(86) PCT No.: PCT/JP2015/069100
§ 371 (c)(1),
(2) Date: Mar. 1, 2017

(87) PCT Pub. No.: WO2016/047231
PCT Pub. Date: Mar. 31, 2016

(65) Prior Publication Data
US 2017/0306160 A1    Oct. 26, 2017

(30) Foreign Application Priority Data

Sep. 26, 2014 (JP) .................................. 2014-197082

(51) Int. Cl.
| | | |
|---|---|---|
| C09C 1/00 | (2006.01) | |
| C08K 3/22 | (2006.01) | |
| C09D 7/40 | (2018.01) | |
| A61K 8/26 | (2006.01) | |
| A61Q 1/02 | (2006.01) | |
| C09C 1/62 | (2006.01) | |
| C09C 3/06 | (2006.01) | |
| C09D 201/00 | (2006.01) | |
| A61K 8/02 | (2006.01) | |
| A61K 8/19 | (2006.01) | |
| A61K 8/25 | (2006.01) | |
| A61Q 19/00 | (2006.01) | |
| C08K 3/08 | (2006.01) | |
| C08K 3/36 | (2006.01) | |
| C08K 7/00 | (2006.01) | |
| C08K 9/02 | (2006.01) | |
| C09D 5/36 | (2006.01) | |
| A61Q 3/02 | (2006.01) | |
| A61Q 5/00 | (2006.01) | |

(52) U.S. Cl.
CPC .......... C09C 1/0078 (2013.01); A61K 8/0262 (2013.01); A61K 8/0266 (2013.01); A61K 8/19 (2013.01); A61K 8/25 (2013.01); A61K 8/26 (2013.01); A61Q 1/02 (2013.01); A61Q 3/02 (2013.01); A61Q 5/00 (2013.01); A61Q 19/00 (2013.01); C08K 3/08 (2013.01); C08K 3/22 (2013.01); C08K 3/36 (2013.01); C08K 7/00 (2013.01); C08K 9/02 (2013.01); C09C 1/62 (2013.01); C09C 3/06 (2013.01); C09D 5/36 (2013.01); C09D 7/40 (2018.01); C09D 201/00 (2013.01); A61K 2800/10 (2013.01); A61K 2800/436 (2013.01); A61K 2800/621 (2013.01); A61K 2800/63 (2013.01); A61K 2800/651 (2013.01); C08K 2003/0806 (2013.01); C08K 2003/0812 (2013.01); C08K 2003/2231 (2013.01); C08K 2201/005 (2013.01); C09C 2200/1058 (2013.01); C09C 2200/24 (2013.01); C09C 2200/502 (2013.01); C09C 2220/103 (2013.01)

(58) Field of Classification Search
CPC ...... A61K 2800/436; A61K 8/19; A61K 8/25; A61Q 1/10; A61Q 3/02; A61Q 9/00; C01P 2006/64; C09C 1/0015; C09C 1/0021; C09C 1/62; C09C 1/642; C09C 2200/24; C09C 2200/502; C09C 2220/106; C09D 11/03
See application file for complete search history.

(56) References Cited

U.S. PATENT DOCUMENTS

| | | |
|---|---|---|
| 6,783,584 B2 | 8/2004 | Takahashi |
| 7,998,266 B2 * | 8/2011 | Morimitsu ............... A61K 8/19 106/14.05 |
| 2003/0017316 A1 | 1/2003 | Pfaff et al. |

(Continued)

FOREIGN PATENT DOCUMENTS

| | | |
|---|---|---|
| CN | 1312840 A | 9/2001 |
| CN | 1774469 A | 5/2006 |

(Continued)

Primary Examiner — Shuangyi Abu Ali
(74) Attorney, Agent, or Firm — Birch, Stewart, Kolasch & Birch, LLP

(57) ABSTRACT

A colored metallic pigment according to the present invention is a colored metallic pigment including at least a metallic pigment, an amorphous silicon oxide film layer formed on a surface of the metallic pigment, a metallic-particle-supporting layer formed on a surface of the amorphous silicon oxide film layer, and metallic particles formed on a surface of the metallic-particle-supporting layer, characterized in that the metallic-particle-supporting layer is formed of one or both of a metal layer and a metal oxide layer composed of a metal oxide other than silicon oxide, the metallic particles are formed to directly cover a part of the surface of the metallic-particle-supporting layer, and the amorphous silicon oxide film layer has a thickness of more than 500 nm.

7 Claims, No Drawings

(56) References Cited

U.S. PATENT DOCUMENTS

| | | |
|---|---|---|
| 2003/0209169 A1 | 11/2003 | Andes et al. |
| 2004/0180010 A1* | 9/2004 | Andes .................. C09C 1/0015 424/63 |
| 2005/0147821 A1 | 7/2005 | Hashizume et al. |
| 2007/0026224 A1 | 2/2007 | Seeger et al. |
| 2008/0318012 A1* | 12/2008 | Domnick .............. C09C 1/0015 428/216 |
| 2009/0017082 A1 | 1/2009 | Morimitsu et al. |
| 2010/0137488 A1 | 6/2010 | Kitamura et al. |
| 2012/0296026 A1 | 11/2012 | Hashizume et al. |
| 2013/0131187 A1 | 5/2013 | Hashizume et al. |

FOREIGN PATENT DOCUMENTS

| | | |
|---|---|---|
| CN | 101384674 A | 3/2009 |
| CN | 101426861 A | 5/2009 |
| CN | 102741181 A | 10/2012 |
| CN | 103025832 A | 4/2013 |
| JP | 2002-522618 A | 7/2002 |
| JP | 2003-131029 A | 5/2003 |
| JP | 2003-292825 A | 10/2003 |
| JP | 2012-31232 A | 2/2012 |
| WO | WO 2007/094253 A1 | 8/2007 |

* cited by examiner

COLORED METALLIC PIGMENT

CROSS REFERENCE TO RELATED APPLICATIONS

This application is the National Phase of PCT/JP2015/069100 filed on Jul. 2, 2015, which claims priority under 35 U.S.C. § 119(a) to Patent Application No. 2014-197082 filed in Japan on Sep. 26, 2014, all of which are hereby expressly incorporated by reference into the present application.

TECHNICAL FIELD

The present invention relates to a colored metallic pigment.

BACKGROUND ART

As for a colored metallic pigment having a metallic feeling excellent in design performance, a colored metallic pigment produced by adhering a colored pigment onto a metallic pigment is known heretofore. In the colored metallic pigment, an organic pigment such as a diketopyrrolopyrrole type, a quinacridon type, a dioxazine type, an isoindolinone type, a condensed azo type, a thren type, a perinone type, a perylene type, a phthalone type, a phthalocyanine type or the like, or an inorganic pigment such as iron oxide or carbon black is used as the colored pigment to be adhered onto the metallic pigment.

However, the colored metallic pigment as mentioned above has such a disadvantage that a colored pigment adhered onto the surface of a metallic pigment is easily optically deteriorated by the reflection of light on the surface of the metallic pigment. For overcoming this disadvantage, it is necessary to select a pigment having relatively superior light resistance, such as phthalocyanine green, phthalocyanine blue and iron oxide, and therefore it is the today's situation that the design performance of the resultant colored metallic pigment is restricted.

Meanwhile, with respect to a pearlescent pigment such as mica, a pigment produced by forming a covering film of silicon oxide, titanium oxide, a metal or the like on the surface of a pigment to impart an interference color to the pigment is known. However, the pearlescent pigment has such a disadvantage that the hiding power is poor and therefore the pearlescent pigment cannot hide an under layer satisfactorily when the pearlescent pigment is compounded to a paint or an ink. For the purpose of avoiding this disadvantage, a metallic pigment that is colored by being covered with an interference film made of silicon oxide, aluminum oxide, titanium oxide or the like has been disclosed as a metallic pigment having high hiding power. However, these pigments are insufficient as means for overcoming the disadvantage.

A colored metallic pigment disclosed in WO2007/094253 (PTD 1) has a constitution comprising a metallic pigment, an amorphous silicon oxide film layer formed on a surface of the metallic pigment, a metal layer formed on a surface of the amorphous silicon oxide film layer, and metallic particles formed on a surface of the metal layer, and this constitution enables the achievement of good design performance.

Further, a colored metallic pigment disclosed in Japanese Patent Laying-Open No. 2012-031232 (PTD 2) has a constitution comprising a metallic pigment, an amorphous silicon oxide film layer formed on a surface of the metallic pigment, a metal oxide layer composed of a metal oxide other than silicon oxide, and metallic particles formed on a surface of the metal oxide layer, and this constitution also enables the achievement of good design performance.

CITATION LIST

Patent Document

PTD 1: WO2007/094253
PTD 2: Japanese Patent Laying-Open No. 2012-031232

SUMMARY OF INVENTION

Technical Problem

The colored metallic pigments disclosed in PTD 1 and PTD 2 both have a characteristic that the color tone changes as it is observed with a viewing angle being changed. In recent years, however, there has been a demand for colored metallic pigments having a greater change in color tone.

The colored metallic pigments of PTD 1 and PTD 2 develop a color according to the following mechanism. Specifically, the amorphous silicon oxide film layer and the metal layer or the metal oxide layer are formed on the surface of the metallic pigment serving as a base material. Mainly, of light incident from the surface of the colored metallic pigment, a part of the light is reflected on the surface of the colored metallic pigment without entering these layers (first reflected light), whereas the remaining light is refracted in these layers and reflected on the surface of the metallic pigment serving as a base material (or at an interface between the layers) (second reflected light). Therefore, when the light is incident on the surface of the colored metallic pigment, optical paths of these two reflected lights have different lengths (optical path difference), causing a phase difference between wavelengths of the lights. Consequently, light of a specific wavelength is emphasized and develops a color.

However, in order to produce a greater change in color tone depending on the viewing angle, it is necessary to increase the optical path difference mentioned above because the change in color tone depends on the optical path difference. For that purpose, it is necessary to increase the thickness of the layers.

The present invention has been made in the above-mentioned situations, and an object of the present invention is to provide a colored metallic pigment that develops a greater change in color tone than ever before depending on the viewing angle.

Solution to Problem

A colored metallic pigment according to the present invention is a colored metallic pigment including at least a metallic pigment, an amorphous silicon oxide film layer formed on a surface of the metallic pigment, a metallic-particle-supporting layer formed on a surface of the amorphous silicon oxide film layer, and metallic particles formed on a surface of the metallic-particle-supporting layer, characterized in that the metallic-particle-supporting layer is formed of one or both of a metal layer and a metal oxide layer composed of a metal oxide other than silicon oxide, the metallic particles are formed to directly cover a part of the surface of the metallic-particle-supporting layer, and the amorphous silicon oxide film layer has a thickness of more than 500 nm.

Preferably, the amorphous silicon oxide film layer has a thickness within a range of more than 500 nm and less than or equal to 1000 nm, and the metallic particles have an average particle size of less than or equal to 50 nm.

Preferably, the metal layer contains at least one selected from the group consisting of Sn, Pd, Pt, and Au, and the metal oxide layer contains an oxide of at least one element selected from the group consisting of Mg, Sn, Zn, Co, Ni, Fe, Zr, Ti, and Ce. Preferably, the metallic particles contain at least one element selected from the group consisting of Cu, Ni, and Ag.

The present invention also relates to a resin composition containing at least the colored metallic pigment according to any of the above descriptions, and to an applied object having the resin composition applied on a base body.

The present invention also relates to a cosmetic containing at least the colored metallic pigment according to any of the above descriptions.

Advantageous Effects of Invention

Since the colored metallic pigment according to the present invention has the above-mentioned constitution and in particular the amorphous silicon oxide film layer formed on the surface of the metallic pigment has a thickness of more than 500 nm, the colored metallic pigment has an excellent effect that a greater change in color tone than ever before depending on the viewing angle can be achieved.

DESCRIPTION OF EMBODIMENTS

The present invention is described below in detail.
<Colored Metallic Pigment>

The colored metallic pigment according to the present invention includes at least a metallic pigment, an amorphous silicon oxide film layer formed on a surface of the metallic pigment, a metallic-particle-supporting layer formed on a surface of the amorphous silicon oxide film layer, and metallic particles formed on a surface of the metallic-particle-supporting layer, characterized in that the metallic-particle-supporting layer is one or both of a metal layer and a metal oxide layer composed of a metal oxide other than silicon oxide, the metallic particles are formed to directly cover a part of the metallic-particle-supporting layer, and the amorphous silicon oxide film layer has a thickness of more than 500 nm.

That is, in the colored metallic pigment according to the present invention, the metallic particles are not formed as a layer that entirely covers the metallic-particle-supporting layer and the metallic pigment (i.e., base material). Therefore, there are a region that is covered with the metallic particles and a region that is not covered with the metallic particles. Thus, since the metallic particles are formed to partially cover the metallic pigment (i.e., base material) as mentioned above, of reflected light coming from the metallic pigment, only a part thereof which passes through spaces between the metallic particles is recognized as visible light. As a result, reflective brightness from the metallic pigment is weakened and chroma (i.e., color) is developed. Further, the colored metallic pigment according to the present invention has characteristics that an interference color having high chroma is developed as the result of the interference between reflected light coming from the surface of the metallic pigment (i.e., base material) and reflected light coming from the surfaces of the metallic particles, and that a change in color tone depending on the viewing angle is significantly great due to a large thickness of the amorphous silicon oxide film layer.

In the present invention, since the metallic particles are formed to directly cover a part of the metallic-particle-supporting layer, the detachment of the metallic particles can be prevented due to good adhesion between the metallic-particle-supporting layer and the metallic particles and, therefore, a colored metallic pigment having a wide variety of colors and a changeful interference color can be obtained in a stable manner.

The colored metallic pigment according to the present invention is obtained by forming at least the amorphous silicon oxide film layer, the metallic-particle-supporting layer and the metallic particles on the surface of the metallic pigment. Therefore, the colored metallic pigment is advantageous because the colored metallic pigment can be produced by relatively simple means and can be imparted with a good finish appearance.

The colored metallic pigment according to the present invention enables the formation of a resin composition having an excellent finish appearance when used in various paints and inks. The colored metallic pigment can be particularly suitably used for a water-based paint and ink. Further, the colored metallic pigment according to the present invention can provide a cosmetic that can develop a clear color when the colored metallic pigment is used in the cosmetic. As mentioned above, the colored metallic pigment according to the present invention can be extremely usefully used in industrial applications.

<Metallic Pigment>

Preferred examples of the metallic pigment to be used in the present invention include aluminum, copper, zinc, titanium, iron, nickel, chromium and alloys thereof, metal-covered flaky glass and other metal-covered inorganic pigments. Among these pigments, aluminum is particularly preferably used from the viewpoint of design performance. The use of aluminum is advantageous, because a wide variety of colored metallic pigments capable of developing an interference color can be obtained by forming the amorphous silicon oxide film layer thereon and superposing the metallic particles on the amorphous silicon oxide film layer.

The preferred average particle size of the metallic pigment falls, for example, within the range from 2 to 300 μm. When the average particle size is greater than or equal to 2 μm, a colored metallic pigment that can impart a good finish appearance and good hiding power to a coating film can be obtained. When the average particle size is smaller than or equal to 300 μm, a colored metallic pigment that can prevent the deterioration in the finish appearance of the coating film caused by insufficient dispersion of the colored metallic pigment can be obtained. More preferably, the average particle size falls within the range from 5 to 100 μm. The term "average particle size of the metallic pigment" as used herein means an average longer length of the metallic pigment. The average particle size can be measured by a laser diffraction method.

The shape of the metallic pigment is not particularly limited, and the metallic pigment can take a variety of shapes such as a spherical shape, a granular shape, a polygonal shape, an indefinite shape, a block shape, and a flaky shape. Among these shapes, the flaky shape is preferable from the viewpoint that a good design performance and a wide variety of colors can be obtained.

When the metallic pigment has a flaky shape, the preferred thickness (average thickness) thereof falls, for example, within the range from 0.01 to 5 μm. When the thickness is greater than or equal to 0.01 µm, a colored metallic pigment that can retain the finish appearance thereof at a good level without deteriorating the light resistance and weather resistance of the coating film can be obtained. When the thickness is less than or equal to 5 µm, a colored metallic pigment that can impart a good design performance and a wide variety of colors to the coating film can be obtained. More preferably, the thickness falls within the range from 0.02 to 1 µm. The thickness can be measured by a water surface diffusion area method (thickness=4000/S µm, wherein S represents a water surface diffusion area ($cm^2/g$)).

As mentioned above, the preferred shape of the metallic pigment is a flaky (i.e., scale-like) shape, wherein the ratio of an average particle size A to an average thickness B (i.e., A/B) preferably falls within the range from 5 to 1000. When the A/B ratio is greater than or equal to 5, the coating film can have a good design performance and a wider variety of colors can be developed. When the A/B ratio is less than or equal to 1000, the metallic pigment is rarely deformed during the production of the colored metallic pigment and the dispersibility of the colored metallic pigment in the resin composition is rarely deteriorated, which is preferred. More preferably, the A/B ratio falls within the range from 15 to 500. The shape of the metallic pigment is particularly preferably a coin-like shape having a smooth surface and a round edge face.

The metallic pigment to be used in the present invention can be obtained in the form of a powder that is produced by an atomizing method, a powder that is produced by grinding metal flakes by a wet ball milling method (i.e., hole method) or a dry ball milling method, or the like. The metallic pigment can also be obtained by depositing a metal thin film on a film or the like, then delaminating the metal thin film and grinding the metal thin film. The metal-covered flaky glass and other metal-covered pigments can be obtained by forming an element metal such as Ag, Cu, Ni, Fe, Co, Cr or Sn or an alloy of the metal in the form of a layer on a flaky or granular inorganic base material such as flaky glass, mica, alumina, silica or titanium oxide by a technique such as electroless plating, deposition and sputtering.

With respect to the metallic pigment, an under layer may be formed thereon using a molybdenum compound, a phosphorus compound, aqueous hydrogen peroxide or the like prior to the formation of the amorphous silicon oxide film layer thereon. In the present invention, even when the under layer is formed on the surface of the metallic pigment, it is described as "the amorphous silicon oxide film layer is formed on the surface of the metallic pigment". Further, a weather-resistant coating layer may be additionally formed on the metallic particles. Examples of the weather-resistant coating layer include a single film containing an oxide, a hydroxide or a hydrate each containing at least one element selected from the group consisting of aluminum, silicon and cerium, a mixture film containing a mixture of the oxide, the hydroxide or the hydrate, and a resin covering layer.

<Amorphous Silicon Oxide Film Layer>

In the colored metallic pigment according to the present invention, an amorphous silicon oxide film layer (layer formed from amorphous silicon oxide) having a layer thickness of more than 500 nm is formed on the surface of the metallic pigment. The amorphous silicon oxide film layer is preferably formed on the entire surface of the metallic pigment. A case in which the surface of the metallic pigment contains a region on which the amorphous silicon oxide film layer is not formed does not depart from the scope of the present invention, as long as the effect of the present invention can be achieved. The amorphous silicon oxide film layer may be directly formed on the surface of the metallic pigment. However, it is preferred that another layer is interposed as an under layer between the metallic pigment and the amorphous silicon oxide film layer. An example of the under layer is, but is not limited to, a layer that includes a single film containing any one of an oxide, a hydroxide or a hydrate each containing at least one element selected from the group consisting molybdenum, phosphorous and aluminum, or a mixture film containing a mixture of the oxide, the hydroxide or the hydrate, as mentioned below. The under layer may contain one layer, or two or more layers. When the under layer contains two or more layers, layers each having a different composition may be stacked on each other.

In the present invention, by forming the amorphous silicon oxide film layer, an effect of imparting a given refractive index and developing an interference color can be achieved. Further, by setting the layer thickness thereof to more than 500 nm, a change in color tone becomes greater than ever before. As for the method for forming the amorphous silicon oxide film layer, a method in which the metallic pigment and a solution containing an organosilicon compound are stirred or kneaded in the form of a slurry or a paste while keeping the atmosphere basic or acidic, or the like may be employed. In this manner, the amorphous silicon oxide film layer can be formed on the surface of the metallic pigment or on the surface of the metallic pigment having the under layer formed on the surface thereof.

Examples of the above-mentioned organosilicon compound include methyltriethoxysilane, methyltrimethoxysilane, tetraethoxysilane, tetramethoxysilane, tetraisopropoxysilane and condensation products thereof, γ-aminopropyltriethoxysilane, N-2-aminoethyl-3-aminopropyltriethoxysilane, and N-2-aminoethyl-3-aminopropylmethyldimethoxysilane.

As for the solvent in which a silicon compound is to be dissolved to prepare the solution containing the organosilicon compound, a hydrophilic solvent is preferably used, such as methyl alcohol, ethyl alcohol, isopropyl alcohol, n-propyl alcohol, t-butyl alcohol, n-butyl alcohol, isobutyl alcohol, ethyl cellosolve, butyl cellosolve, propylene glycol monobutyl ether, dipropylene glycol monomethyl ether, propylene glycol monopropyl ether, and acetone. It is desirable to further compound water to the solvent in a sufficient amount for hydrolyzing alkoxysilane.

In this manner, the amorphous silicon oxide film layer can be formed on the surface of the metallic pigment by hydrolyzing the organosilicon compound in a solvent mainly containing the hydrophilic solvent having the metallic pigment dispersed therein to allow amorphous silicon oxide to be deposited on the metallic pigment.

The thickness of the amorphous silicon oxide film layer should be more than 500 nm. When the thickness is more than 500 nm, an optical path difference for developing an interferential action is increased, and thus a coating film that presents higher chroma and a greater change in color tone than ever before can be formed. Although the upper limit of the thickness is not particularly limited, if the amorphous silicon oxide film layer is too thick, it takes a longer time to form the amorphous silicon oxide film layer and thereby productivity may be reduced. In addition, since the total thickness of the colored metallic pigment is increased, the resultant coating film may have poor smoothness. From such a viewpoint, the thickness is preferably less than or equal to 1000 nm. The thickness of the amorphous silicon oxide film layer can be measured by the observation of a cross section using a scanning electron microscope. In this case, such measurement is performed on any 50 pieces of the colored metallic pigment, and the average value thereof is determined as the thickness of the amorphous silicon oxide film layer.

As mentioned above, in the colored metallic pigment according to the present invention, when the thickness of the amorphous silicon oxide film layer falls within the range exceeding 500 nm and the average particle size of the below-mentioned metallic particles is less than or equal to 50 nm, an effect of developing an interference color having particularly high chroma and a great change in color tone can be achieved.

The term "amorphous" as used herein with respect to the amorphous silicon oxide film layer means that no clear diffraction peak derived from silicon oxide is detected in the analysis of the crystal structure of the amorphous silicon oxide film layer by an X-ray diffraction method.

<Metallic-Particle-Supporting Layer>

In the present invention, a metallic-particle-supporting layer is formed on the surface of the amorphous silicon oxide film layer mentioned above. The metallic-particle-supporting layer is preferably formed on the entire surface of the amorphous silicon oxide film layer. The surface of the amorphous silicon oxide film layer may have a region on which the metallic-particle-supporting layer is not formed as a part thereof, and this embodiment does not depart from the scope of the present invention as long as the embodiment can achieve the effect of the present invention.

Such a metallic-particle-supporting layer is formed of one or both of a metal layer and a metal oxide layer composed of a metal oxide other than silicon oxide. When the metallic-particle-supporting layer is formed of both of a metal layer and a metal oxide layer, the order of stacking these layers is not particularly limited. Specifically, the metallic-particle-supporting layer may have a constitution in which the metal layer is stacked on the surface of the amorphous silicon oxide film layer and the metal oxide layer is stacked on the surface of the metal layer, or may have a constitution in which the metal oxide layer is stacked on the surface of the amorphous silicon oxide film layer and the metal layer is stacked on the surface of the metal oxide layer. Further, the metallic-particle-supporting layer can also include two or more metal layers and/or two or more metal oxide layers, and the order of stacking these layers in that case is not particularly limited, either.

Each of the metal layer and the metal oxide layer is described below in detail.

<Metal Layer>

When the metallic particles in the present invention are formed by electroless plating using a water-soluble metal salt, the metal layer can be formed by a method employed as a pretreatment for the electroless plating. The pretreatment for the electroless plating generally includes the catalyst (also referred to as catalyzing)-accelerator (also referred to as accelerating) process and the sensitizing-activating process, and either process may be employed. Further, only the catalyst process or the sensitizing process may be performed.

The catalyst-accelerator process is a method employing a mixed solution containing Sn and any one of Pd, Pt and Au as a catalyst, dipping the metallic pigment having the amorphous silicon oxide film layer formed thereon in this catalyst, adsorbing a complex compound of any one of Pd, Pt and Au and Sn or the like to the surface of the amorphous silicon oxide film layer, thereafter employing an acidic solution such as sulfuric acid or hydrochloric acid or an alkaline solution such as sodium hydroxide or ammonia as an accelerator, dipping the aforementioned metallic pigment in this accelerator, removing Sn and activating any one of Pd, Pt and Au.

The sensitizing-activating process is a method employing an Sn solution as a sensitizing liquid, dipping the metallic pigment having the amorphous silicon oxide film layer formed thereon in this sensitizing liquid, adsorbing Sn to the surface of the amorphous silicon oxide film layer, thereafter employing a solution containing any one of Pd, Pt and Au as an activating solution and supporting any one of Pd, Pt and Au on the surface of the aforementioned amorphous silicon oxide film layer.

The sensitizing process is a method employing an Sn solution as a sensitizing liquid and dipping the metallic pigment having the amorphous silicon oxide film layer formed thereon in this sensitizing liquid for adsorbing Sn to the surface of the amorphous silicon oxide film layer, thereby supporting Sn on the surface of the amorphous silicon oxide film layer.

A water-soluble metal salt containing any one of Sn, Pd, Pt and Au can be used as a metal source for the metal layer formed in the method employed as the pretreatment for the electroless plating. Tin chloride, tin oxalate, tin sulfate, tin bromide, tin acetate, tin borofluoride, tin fluoride, sodium stannate, potassium stannate, tin methanesulfonate, tin sulfide, tin silicofluoride, palladium chloride, palladium acetate, palladium bromide, palladium hydroxide, palladium nitrate, palladium oxide, palladium sulfate, gold bromide, gold chloride, platinum chloride, platinum oxide or the like can be illustrated as a specific metal salt.

According to the aforementioned method, a catalyst layer of Sn, Pd, Pt, Au or the like is supported as the metal layer in the present invention. Thereafter the metallic particles can be formed on the surface of this metal layer by electroless plating. When the metallic pigment having the metal layer formed thereon is dipped in an electroless plating solution, a reducing agent in the plating solution is oxidized on the surface of the metal layer due to catalytic activity of the metal layer. Metallic ions in the electroless plating solution are reduced by electrons emitted at this time, the metal is deposited on the surface of the metal layer, and the metallic particles are formed.

Preferably, the metal layer contains at least one selected from the group consisting of Sn, Pd, Pt, and Au, as mentioned above.

In the present invention, the thickness of the metal layer is preferably less than or equal to 30 nm. In this case, the resultant colored metallic pigment can be imparted with better chroma and interference color. The thickness of the metal layer is more preferably set to a value falling within the range from 0.1 to 10 nm. The thickness of the metal layer can be confirmed as the layer of metal formed between the amorphous silicon oxide film layer and the metallic particles in high magnification observation of about 3 million magnifications in a transmission electron microscope (TEM), for example. Presence of the element can also be confirmed by local EDS (energy-dispersive X-ray spectroscopy). The metal layer is typically formed by a continuous layer of aggregates of particles.

The metal layer may be uniformly or non-uniformly deposited on the surface of the amorphous silicon oxide film layer (or the metal oxide layer mentioned below). Even if the thickness of the metal layer is so small that the same cannot be observed with a TEM, for example, the metallic particles can be densely and uniformly deposited when the metal layer is deposited.

<Metal Oxide Layer>

In the present invention, a metal oxide layer composed of a metal oxide other than silicon oxide is formed on the surface of the amorphous silicon oxide film layer (in the case where the metal layer is previously formed, on the surface of the metal layer; the same applies hereinafter). The metal oxide layer is preferably formed on the entire surface of the amorphous silicon oxide film layer. The surface of the amorphous silicon oxide film layer may have a region on which the metal oxide layer is not formed as a part thereof, and this embodiment does not depart from the scope of the present invention as long as the embodiment can achieve the effect of the present invention. By forming the metal oxide layer, the adsorption state of the below-mentioned metallic particles onto the metal oxide layer becomes good, the metallic particles can be densely and uniformly deposited with a regular spacing, and an interference color having high chroma can be developed.

The metal oxide layer preferably contains an oxide of at least one element selected from the group consisting of Mg (magnesium), Sn (tin), Zn (zinc), Co (cobalt), Ni (nickel), Fe (iron), Zr (zirconium), Ti (titanium) and Ce (cerium), particularly preferably a metal oxide of any one of Sn, Zn, Ti and Ce.

The method for forming the metal oxide layer is not particularly limited. Preferred examples of the method to be employed include: a method of hydrolyzing an alkoxide of a metal that constitutes the metal oxide layer by a sol-gel method to allow the metal oxide layer to be deposited on the amorphous silicon oxide film layer; a method of adding an alkali to a metal salt solution of a metal that constitutes the metal oxide layer to allow the metal oxide to be deposited by neutralization; and a method of bringing the metallic pigment having the amorphous silicon oxide film layer formed thereon into contact with a solution in which an organic metal compound has been dissolved in an organic solvent and then subjecting the resultant product to a heat treatment to oxidize the organic metal compound, thereby forming the metal oxide layer on the amorphous silicon oxide film layer.

Examples of the metal alkoxide to be used in the method of depositing the metal oxide layer by hydrolysis include tetraethoxytin and tetrabutoxytitanium, and a colloid solution having the metal alkoxide dispersed therein can be preferably used. Examples of a catalyst for the hydrolysis of the metal alkoxide include aqueous ammonia, ethylene diamine, monoethanolamine, diethanolamine, hydrazine, and urea.

Examples of a metal salt to be used in the method of depositing the metal oxide layer by neutralization include tin chloride, tin fluoride, zinc chloride, titanyl sulfide, cerium nitrate, and cerium acetate. Examples of a neutralizing agent for the metal salt include aqueous ammonia, sodium hydroxide, monoethanolamine, and diethanolamine. Examples of a reaction solvent include water, ethanol, isopropyl alcohol, methyl propylene glycol, and butyl cellosolve.

Examples of the organic metal compound to be used in the method using the organic metal compound include fatty acid metal salts such as cobalt naphthenate, nickel stearate, zirconium stearate, and dibutyltin dilaurate. As for a solvent for dissolving the organic metal compound therein, any organic solvent in which the organic metal compound can be dissolved can be used, such as toluene, xylene, dimethylformamide, acetone, ethyl acetate, isopropyl alcohol, propylene glycol monomethyl ether, and butyl cellosolve. The heat treatment temperature at which the organic metal compound is to be decomposed and oxidized is preferably 200° C. to 500° C. If the heat treatment temperature is lower than or equal to 200° C., it is difficult to oxidize the organic metal compound. If the heat treatment temperature is higher than or equal to 500° C., the aggregation of the metallic pigment may occur readily and the risk of ignition increases.

When the metallic particles of the present invention are formed by electroless plating using a water-soluble metal salt, a layer containing Sn, Pt, Au, Pd, Zn or the like, which is generally used as a pretreatment for the electroless plating, may be formed on the metal oxide layer. Even when the layer is formed, it is described in the present invention as "the metallic particles are formed to directly cover the metal oxide layer (the metallic-particle-supporting layer)".

In the present invention, when the metal oxide layer is provided between the amorphous silicon oxide film layer and the pretreatment layer for the electroless plating, the adhesion force of the metallic particles is stronger than that achieved by a conventional method and the color tone stability against mechanical, thermal or chemical attacks is excellent. Further, it is possible to achieve the development of a different color from those in the conventional method by forming the metal oxide layer on the amorphous silicon oxide film layer.

In the present invention, the thickness of the metal oxide layer is preferably less than or equal to 30 nm. In this case, the resultant colored metallic pigment can be imparted with better chroma and interference color. The thickness of the metal oxide layer is more preferably set to a value falling within the range from 0.1 to 10 nm. The metal oxide layer may be uniformly or non-uniformly deposited on the surface of the amorphous silicon oxide film layer. If the metal oxide layer is too thick, the thickness of the resultant colored metallic pigment is also increased and the hiding power of the resultant colored metallic pigment is deteriorated. If the metal oxide layer is too thin, the effect cannot be satisfactorily achieved and the color tone is unstable. The thickness of the metal oxide layer can be measured by the observation of a cross section using a transmission electron microscope (TEM).

<Metallic Particles>

In the colored metallic pigment according to the present invention, metallic particles are formed on the surface of the metallic-particle-supporting layer. The metallic particles are characterized by being formed to directly cover a part of the surface of the metallic-particle-supporting layer.

The colored metallic pigment according to the present invention has a region on which the metallic particles are not formed, i.e., a region which is not covered with the metallic particles. By employing this constitution, interference occurs between reflected light coming from the surfaces of the metallic particles and reflected light passing through the amorphous silicon oxide film layer and coming from the surface of the metallic pigment (base material) and, therefore, a colored metallic pigment having an interference color with high chroma can be obtained. Further, since the metallic particles are directly formed on the surface of the metallic-particle-supporting layer, the adhesion between the metallic-particle-supporting layer and the metallic particles becomes good and it becomes possible to certainly obtain a colored metallic pigment having a wide variety of colors and a changeful interference color.

Preferred examples of the metallic particles to be used in the present invention include particles containing at least one component selected from the group consisting of Al (aluminum), Ti (titanium), Cr (chromium), Fe (iron), Co (cobalt), Ni (nickel), Cu (copper), Zn (zinc), Ru (ruthenium), Rh (rhodium), Pd (palladium), Ag (silver), Sn (tin), Pt (platinum), Au (gold) and alloys thereof. When the metallic particles contain at least one component selected from the metals and the metal alloys, a colored metallic pigment that develops an interference color having high chroma can be obtained. Particularly preferred examples of the metallic particles include particles containing at least one element selected from the group consisting of Cu, Ni, and Ag.

The metallic particles preferably have an average particle size of less than or equal to 50 nm. In this case, the surface of the colored metallic pigment having both a region on which the metallic particles are formed and a region on which the metallic particles are not formed is relatively smooth and, therefore, it becomes possible to obtain a colored metallic pigment that can provide a metallic film having an excellent finish appearance. The average particle size of the metallic particles is more preferably less than or equal to 30 nm. The lower limit of the average particle size of the metallic particles is not particularly limited, and is preferably greater than or equal to 1 nm. If the average particle size is less than 1 nm, light can pass through the metallic particles, reflected light coming from the layer of the metallic particles is reduced, and the coloring effect by the light interference is weakened, sometimes leading to the decrease in chroma of the resultant colored metallic pigment.

In the colored metallic pigment according to the present invention, it is particularly preferred that the amorphous silicon oxide film layer has a thickness within a range of more than 500 nm and less than or equal to 1000 nm and the metallic particles have an average particle size of less than or equal to 50 nm. In this case, an interference color having particularly high chroma can be obtained and a great change in color tone can be developed depending on the viewing angle.

The metallic particles formed in the colored metallic pigment according to the present invention are formed to cover a part of the metallic-particle-supporting layer, rather than entirely cover the metallic-particle-supporting layer. It is preferred that the spacing between the metallic particles is less than or equal to 10 nm, because a colored metallic pigment having higher chroma can be obtained. In this case, the spacing between the metallic particles, which is defined as having a size of less than or equal to 10 nm, corresponds to the region that is not covered with the metallic particles mentioned above. In this case, the lower limit value of the spacing is preferably greater than or equal to 0.1 nm.

In the present invention, the metallic particles may be deposited in such a manner that two or more particles of the metallic particles are overlaid on the metallic-particle-supporting layer. However, it is preferred that the metallic particles are deposited in the form of a single layer of which the thickness corresponds to the size of a single particle. In this case, an interference color having high chroma can be imparted as the result of the interference between reflected light coming from the metallic particles and reflected light reflected from the metallic pigment (i.e., base material) and passing through spaces between the metallic particles. Further, it is also preferred that the metallic particles are deposited on the metallic-particle-supporting layer in such a state that the metallic particles are not in contact with each other. Most typically, the metallic particles are deposited on the metallic-particle-supporting layer in the form of a single layer in such a state that the metallic particles are not in contact with each other and the spacing between the metallic particles is less than or equal to 10 nm.

The state of deposition of the metallic particles, the average particle size of the metallic particles, and the spacing between the metallic particles can be evaluated by, for example, the observation of a cross section using a transmission electron microscope (TEM). In this case, for the preparation of a sample for the observation, a method of subjecting the cross section of the colored metallic pigment having the metallic particles formed thereon to FIB (focused ion beam) processing is preferably employed. This method can determine a part to be processed while viewing a scanning ion microscopy (SIM: scanning ion microscopy) image, and therefore can process a specified part in the sample. The colored metallic pigment is processed by the above-mentioned method, and the cross section of the metallic particles is observed using a transmission electron microscope (TEM) at a 300,000 to 3,000,000-fold magnification.

The method for forming the metallic particles is not particularly limited, and a vacuum deposition method, a sputtering method, an electroless plating method or the like can be suitably employed. Among these methods, the electroless plating method is particularly preferred, because this method can deposit the metallic particles uniformly with a predetermined spacing as mentioned above and therefore enables the achievement of good chroma.

<Weather-Resistant Coating Layer or the Like>

In the present invention, a weather-resistant coating layer or the like as mentioned below may be formed on the metallic particles.

1) Weather-resistant coating layer including a single film containing an oxide, a hydroxide or a hydrate, or a mixture film containing a mixture of the oxide, the hydroxide or the hydrate It is preferred that a weather-resistant coating layer that includes a single film containing at least one of an oxide, a hydroxide and a hydrate, or a mixture film containing a mixture of the oxide, the hydroxide or the hydrate is additionally formed. When the weather-resistant coating layer is formed, a discoloration-preventing effect can be imparted to a coating film containing the colored metallic pigment according to the present invention and the weather resistance of the coating film can be improved. Particularly when a metal that easily causes an oxidation reaction or a sulfurization reaction, such as silver and copper, is used for the metallic particles, the formation of the weather-resistant coating layer is effective, because weather resistance can be imparted to the resultant colored metallic pigment. In particular, a layer that contains an oxide, a hydroxide or a hydrate each containing at least one element selected from aluminum, silicon and cerium is preferred.

2) Coupling Agent

Preferably, the metallic particles, or the above-mentioned weather-resistant coating layer in the case where it is formed, is further treated with a coupling agent, particularly a coupling agent containing silicon and/or titanium. In this case, when a coating film is formed from a resin composition containing the colored metallic pigment according to the present invention, a coating resin and so on, an effect of improving the adhesion of the coating film can be achieved as the result of the improvement in the affinity between the colored metallic pigment and the coating resin, and so on. A preferred example of the coupling agent is a silane coupling agent (coupling agent containing silicon). Preferred examples of the silane coupling agent include $R_A$—Si$(OR_B)_3$ and $R_A$—SiR$_B(OR_B)_2$ ($R_A$: alkyl, aryl or alkenyl group having 2 to 18 carbon atoms, $R_B$: alkyl group having 1 to 3 carbon atoms). In these formulae, $R_A$ preferably has a functional group. Examples of the functional group include an amino group, an ureido group, an epoxy group, a sulfide group, a vinyl group, a methacryloxy (methacryl) group, an acryloxy (acryl) group, a mercapto group, and a ketimino group.

Preferred specific examples of the silane coupling agent include methyltriethoxysilane, methyltrimethoxysilane, tetraethoxysilane, tetramethoxysilane, tetraisopropoxysilane, 3-aminopropyl-trimethoxysilane, n-methyl-3-aminopropyl-trimethoxysilane, 3-aminopropyl-triethoxysilane, 3-aminopropyl-tris(2-methoxy-epoxy-silane), n-aminoethyl-3-aminopropyltrimethoxysilane, 3-methacryloxypropyl-trimethoxysilane, 3-acryloxypropyl-trimethoxysilane, 3-glycidyloxypropyl-trimethoxysilane, 3-mercaptopropyl-trimethoxysilane, 3-mercaptopropyl-triethoxysilane, 3-mercaptopropyl-methyldimethoxysilane, vinyltrichlorosilane, vinyltrimethoxysilane, vinyltriethoxysilane, vinyl-tris(2-methoxyethoxy)silane, and condensation products thereof.

A titanium coupling agent (coupling agent containing titanium) can also be used preferably as the coupling agent in the present invention, although the types of the titanium coupling agent are fewer than those of the silane coupling agent. In general, the titanium coupling agent has a hydrolyzable group which is a hydrophilic group and a side-chain organic functional group which is a hydrophobic group. Typically, examples of the hydrolyzable group which is a hydrophilic group include an alkoxyl group, and examples of the side-chain organic functional group which is a hydrophobic group include a phosphoric acid alkyl ester group, an amino group, and a sulfide group. A preferred example of a commercially available product of the titanium coupling agent includes Plenact KR46B produced by Ajinomoto Fine-Techno Co., Inc. For example, Plenact KR46B has such a structure that $C_8H_{17}O$— as a hydrolyzable group and HO—P—$(OC_{13}H_{27})_2$, $C_8H_{17}O$— as side-chain organic functional groups are coordinated with Ti.

3) Resin Covering Layer

In the colored metallic pigment according to the present invention, a resin covering layer may be formed as an outermost layer. In this case, properties, such as chemical resistance, weather resistance, water resistance and moisture resistance, of a coating film that contains the colored metallic pigment can be improved, because the adhesion between the colored metallic pigment according to the present invention and a coating resin can be improved upon the formation of a coating film using a resin composition containing the colored metallic pigment and the coating resin, resulting in the improvement in physical properties of the coating film.

The monomer component constituting the resin covering layer is not particularly limited, and an example is a copolymer synthesized from at least two monomers including, for example, a reactive monomer having a carboxyl group and/or a phosphoric acid group and a polyfunctional (meth) acrylic acid ester monomer having three or more functionalities and/or a polymerizable monomer having a benzene core.

Examples of the reactive monomer having a carboxyl group and/or a phosphoric acid group include acrylic acid, methacrylic acid, maleic acid, crotonic acid, itaconic acid, fumaric acid, 2-methacryloyloxyethyl acid phosphate, di-2-methacryloyloxyethyl acid phosphate, tri-2-methacryloyloxyethyl acid phosphate, 2-acryloyloxyethyl acid phosphate, di-2-acryloyloxyethyl acid phosphate, tri-2-acryloyloxyethyl acid phosphate, diphenyl-2-methacryloyloxyethyl acid phosphate, diphenyl-2-acryloyloxyethyl acid phosphate, dibutyl-2-methacryloyloxyethyl acid phosphate, dibutyl-2-acryloyloxyethyl acid phosphate, dioctyl-2-methacryloyloxyethyl acid phosphate, dioctyl-2-acryloyloxyethyl acid phosphate, 2-methacryloyloxypropyl acid phosphate, bis(2-chloroethyl)vinyl phosphonate, and diallyldibutyl phosphonosuccinate.

Examples of the polyfunctional (meth)acrylic acid ester monomer having three or more functionalities include trimethylolpropane triacrylate, trimethylolpropane trimethacrylate, tetramethylolpropane triacrylate, tetramethylolpropane tetraacrylate, tetramethylolpropane trimethacrylate, tetramethylolpropane tetramethacrylate, pentaerythritol triacrylate, pentaerythritol tetraacrylate, dipentaerythritol hexaacrylate, and ditrimethylolpropane tetraacrylate.

The polyfunctional (meth)acrylic acid ester monomer is involved in the three-dimensional crosslinking of a resin, and has an effect of insolubilizing the resin covering layer against an organic solvent and water.

Examples of the polymerizable monomer having a benzene nucleus include styrene, α-methylstyrene, vinyltoluene, divinylbenzene, phenyl vinyl ketone, phenyl vinyl ether, divinylbenzene monoxide phenoxyethyl acrylate, phenoxy-polyethylene glycol acrylate, and 2-hydroxy-3-phenoxypropyl acrylate.

The copolymerization may be carried out using a monomer as mentioned below besides the above-mentioned monomers. When the below-mentioned monomer is used in the copolymerization, properties such as moisture resistance, weather resistance and adhesion of a coating film produced using the colored metallic pigment according to the present invention can be further improved.

Methyl (meth)acrylate, ethyl (meth)acrylate, n-butyl (meth)acrylate, isobutyl (meth)acrylate, 2-ethylhexyl (meth) acrylate, isodecyl (meth)acrylate, lauryl (meth)acrylate, stearyl (meth)acrylate, butoxy (meth)acrylate, dimethylaminoethyl (meth)acrylate, diethylaminoethyl (meth)acrylate, 2-hydroxybutyl (meth)acrylate, hydroxyethyl (meth)acrylate, 2-hydroxypropyl (meth)acrylate, methoxyethyl (meth) acrylate, butoxyethyl (meth)acrylate, glycidyl (meth)acrylate, cyclohexyl (meth)acrylate, dicyclopentanyloxyethyl (meth)acrylate, dicyclopentanyl (meth)acrylate, tricyclodecane dimethanol di(meth)acrylate, dicyclopentenyloxyethyl (meth)acrylate, dicyclopentenyloxypropyl (meth)acrylate, dicyclopentenyl (meth)acrylate, isobornyl (meth)acrylate, 1-adamantyl (meth)acrylate, 2-methyl-2-adamantyl (meth) acrylate, 1,3-adamantane dimethanol di(meth)acrylate, and esters of other unsaturated carboxylic acids (e.g., acrylic acid, methacrylic acid, crotonic acid, itaconic acid, citraconic acid).

The main constitution of the colored metallic pigment according to the present invention is described above. In the colored metallic pigment, it is only necessary that the metallic-particle-supporting layer and the metallic particles are formed in direct contact with one another, and a layer, a granulated material or the like other than the above-mentioned components may be additionally formed as long as the effect of the present invention cannot be deteriorated.

<Resin Composition>

The present invention also relates to a resin composition such as a paint and an ink, which contains at least the above-mentioned colored metallic pigment. The resin composition in the present invention includes, for example, a paint containing the colored metallic pigment, a coating film thereof, a resin molded object, or an ink and printed matter produced using the ink. Since the colored metallic pigment has a particularly great change in color tone, it can also be used for a resin composition applied or formed on an object to perform authentication. The paint and the ink may be of an organic-solvent-based type or a water-based type.

The amount of the colored metallic pigment to be compounded in the resin composition varies depending on the application purpose and is not particularly limited, and preferably falls within the range from 0.1 to 30 mass % relative to the amount of the resin composition. When the amount to be compounded is greater than or equal to 0.1 mass %, decorative effects including a metallic effect are good. When the amount is less than or equal to 30 mass %, the weather resistance, corrosion resistance, mechanical strength and so on of the resin composition are good. The amount of the colored metallic pigment to be compounded in the resin composition more preferably falls within the range from 1 to 20 mass % relative to the amount of the resin composition. In the case of a resin molded object, the content of the colored metallic pigment may be more than 30 mass % as long as it causes no problem when used.

The resin composition can be obtained, for example, by compounding a coating resin with the colored metallic pigment according to the present invention properly. Examples of the coating resin include an acrylic resin, an alkyd resin, a polyester resin, a polyurethane resin, a polyvinyl acetate resin, a nitrocellulose resin, and a fluororesin.

In the resin composition of the present invention, a colored pigment, an extender pigment, a dye or the like other than the colored metallic pigment may be used in combination, in addition to the colored metallic pigment and the coating resin. Examples of the colored pigment to be used in combination include phthalocyanine, quinacridone, isoindolinone, perylene, azo lake, iron oxide, chrome yellow, carbon black, titanium oxide, and pearl mica.

In the resin composition of the present invention, in addition to the above-mentioned components, an additive such as water, an organic solvent, a surfactant, a curing agent, an ultraviolet ray absorber, a static electricity elimination agent, and a thickening agent may be used, if necessary.

When a coating film is formed using the resin composition of the present invention, the coating film may be formed on an under coating layer or a middle coating layer which is formed by means of electrodeposition coating or the like, and a top-coat layer may be additionally formed on the coating film produced using the resin composition of the present invention.

<Applied Object>

The present invention also relates to an applied object having any of the above-mentioned resin compositions applied on a base body. The material for the base body constituting the applied object is not particularly limited, and may be, for example, metal, resin, wood, paper, leather, or the like.

Examples of the applied object include a vehicle body such as a car and a motorcycle; printed matter such as a lid material, a packing material, a magazine, and a poster; an applied object that needs high security and should be authenticated such as a bill, a passport, a license, and a cash voucher.

<Cosmetic>

The present invention also relates to a cosmetic containing at least the above-mentioned colored metallic pigment.

Heretofore, a pearl pigment and an aluminum pigment have been used for imparting a glossy feeling or brightness to a cosmetic. However, a pearl pigment and an aluminum pigment have the following problems: a pearl pigment has a poor hiding performance; and an aluminum pigment has a gray color and therefore cannot develop a clear color when mixed with a colored pigment. An aluminum pigment has an additional problem that the aluminum pigment easily reacts with water and therefore cannot be used in a water-containing cosmetic.

By compounding the colored metallic pigment according to the present invention, it becomes possible to obtain a cosmetic having excellent hiding power and having a clear color. Further, the colored metallic pigment according to the present invention has such a property that the colored metallic pigment does not react when used in a water-containing cosmetic (i.e., stability).

The cosmetic having the colored metallic pigment according to the present invention compounded is not particularly limited, and examples of specific embodiments of the cosmetic are as follows.

<Embodiments of Cosmetic>

1) The types of the cosmetic include the following items.

Make-up cosmetic (e.g., lipstick, foundation, blush, eye shadow, and nail enamel), hair cosmetic (hair gel, hair wax, hair treatment, shampoo, and hair manicure gel), and basic skin care cosmetic (foundation cream).

2) Examples of the constituent components for the cosmetic other than the colored metallic pigment according to the present invention include the following components.

<Oily Component>

Oils and fats (e.g., olive oil and castor oil), wax (e.g., beeswax, carnauba wax, and lanolin), hydrocarbon oil (e.g., liquid paraffin, squalane, and polybutene), fatty acid ester (e.g., isopropyl myristate, cetyl 2-ethylhexanoate, diisopropyl adipate, and glyceryl trimyristate), higher fatty acid (e.g., oleic acid and isostearic acid), higher alcohol (e.g., isostearyl alcohol and oleyl alcohol), silicone oil (e.g., dimethylpolysiloxane, methylphenylpolysiloxane, and octamethylcyclotetrasiloxane), and fluorine compound (e.g., perfluoro polyether).

<Other Components>

Surfactant, moisturizing agent, polyhydric alcohol, water-soluble polymer, film-forming agent, water-insoluble polymer, polymer emulsion, powder, pigment, dye, lake, lower alcohol, ultraviolet ray absorber, vitamin, antioxidant agent, antibacterial agent, flavoring agent, and water.

<Amount to be Compounded>

In the cosmetic, the colored metallic pigment is compounded in an amount of 0.1 to 99 mass %, preferably 1 to 80 mass %.

3) Preparation Method

Any conventional method for producing a cosmetic can be employed without particular limitation.

As for the method for dispersion, a method using a disper, a method using a roll mill or the like can be employed preferably.

<Method for Producing Colored Metallic Pigment>

The colored metallic pigment according to the present invention can be produced, for example, through the following production steps. That is, the colored metallic pigment can be produced by a production method including at least: a step of hydrolyzing an organosilicon compound in a solvent mainly containing a hydrophilic solvent having a metallic pigment dispersed therein to allow amorphous silicon oxide to be deposited on the metallic pigment, thereby forming an amorphous silicon oxide film layer on the surface of the metallic pigment (amorphous silicon oxide film layer formation step); a step of allowing a metallic-particle-supporting layer to be deposited on the surface of the amorphous silicon oxide film layer, thereby forming the metallic-particle-supporting layer (metallic-particle-supporting layer formation step); and a step of forming metallic particles on the surface of the metallic-particle-supporting layer by an electroless plating method or the like (metallic particle formation step).

In the present invention, when an under layer is formed between the metallic pigment and the amorphous silicon oxide film layer, the under layer is firstly formed on the surface of the metallic pigment. Typically, a method may be employed, in which the metallic pigment and a solution containing a molybdenum compound and/or a phosphorous compound are stirred or kneaded in the state of a slurry or a paste to form a hydration film containing at least one element selected from molybdenum and phosphorous on the metallic pigment and the resultant product is then heated to convert the hydration film into an under layer.

Subsequently, when the under layer is formed as mentioned above, an amorphous silicon oxide film layer is formed on the under layer (amorphous silicon oxide film layer formation step). An organosilicon compound is hydrolyzed in a solvent mainly containing a hydrophilic solvent in which the metallic pigment having the under layer formed thereon is dispersed to allow amorphous silicon oxide to be deposited on the metallic pigment (under layer), thereby forming an amorphous silicon oxide film layer on the surface of the metallic pigment (under layer). As for the hydrophilic solvent, for example, methyl alcohol, ethyl alcohol, isopropyl alcohol, n-propyl alcohol, t-butyl alcohol, n-butyl alcohol, isobutyl alcohol, ethyl cellosolve, butyl cello solve, propylene glycol monobutyl ether, dipropylene glycol monomethyl ether, propylene glycol monopropyl ether, acetone or the like can be used. As for the organosilicon compound, for example, methyltriethoxysilane, methyltrimethoxysilane, tetraethoxysilane, tetramethoxysilane, tetraisopropoxysilane, a condensation product of any one of the above-mentioned compounds, γ-aminopropyltriethoxysilane, N-2-aminoethyl-3-aminopropyltriethoxysilane, N-2-aminoethyl-3-aminopropylmethyldimethoxysilane or the like can be used.

When an alcohol is used as the hydrophilic solvent, the amorphous silicon oxide film layer is formed by forming an alkoxy silicate on the surface of the metallic pigment (under layer), hydrolyzing the alkoxy silicate, and then performing the dehydrative condensation of the resultant product. As for the catalyst for the above-mentioned hydrolysis reaction, an acid or a base can be preferably used.

When a thick amorphous silicon oxide film layer exceeding 500 nm is formed in the present invention, it is preferable to contain an organic compound containing nitrogen (preferably, an organic compound containing an amino group) in a reaction system in the amorphous silicon oxide film layer formation step.

The compound adsorbs (or bonds) to the surface of the amorphous silicon oxide film layer that is under formation in the amorphous silicon oxide film layer formation step. Further, since the compound is present on the surface of the amorphous silicon oxide film layer that is under formation, the organosilicon compound adsorbs starting from the compound, and an amorphous silicon oxide film is readily formed on the surface of the amorphous silicon oxide film layer that is under formation. Although the reason therefor is not known exactly, the reason is assumed to be as follows. Since the compound further adsorbs or bonds to the surface of the amorphous silicon oxide film formed on the surface of the metallic pigment, the compound is incorporated into the amorphous silicon oxide film layer in the amorphous silicon oxide film layer formation step, and the incorporated compound also serves as an adhesive for the amorphous silicon oxide formed on the surface of the metallic pigment, and thereby the amorphous silicon oxide film layer can have a thickness exceeding 500 nm. In particular, when a compound having an amino group is used as the compound, the amino group in the compound also serves as a catalyst for the hydrolysis of the organosilicon compound, and urges the formation of the amorphous silicon oxide film layer on the surface of the metallic pigment.

Examples of the organic compound containing nitrogen include an acid amide (such as urea, dimethylformamide, oleic amide, and stearic acid amide), an amino acid (such as 2-aminobenzoic acid, N-methylglycine, cystine, and phenylalanine), a fatty amine (such as 2-ethylhexylamine, laurylamine, and stearylamine), an alkanolamine (such as 2-dimethylamino ethanol, monoethanolamine, diethanolamine, and triethanolamine), a nitro compound (such as 2-nitropropane and cellulose nitrate), an amino group-containing coupling agent (such as aminophenylsilane, γ-aminopropyltrimethoxysilane, γ-aminopropyltriethoxysilane, N-β-(aminoethyl)-γ-aminopropyltrimethoxysilane, γ-ureidopropyltriethoxysilane, trimethoxysilylpropyldiethylenetriamine, di-n-butoxybis(triethanolaminato) titanium, and N,N-methylethylamino titanate), piperazine, polyethyleneimine, hexamethyldisilazane, and N,O-bis(trimethylsilyl)acetamide. Among these organic compounds containing nitrogen, those containing an amino group are preferable as mentioned above.

Subsequently, a metallic-particle-supporting layer is formed on the surface of the metallic pigment that is covered with the amorphous silicon oxide film layer by the above-mentioned method. Hereinafter, each of the metal layer and the metal oxide layer is described.

First, formation of the metal layer (a metal layer formation step) is described. The metal layer formation step can be carried out as a preceding step of the metallic particle formation step as mentioned below. That is, the metal layer is formed on the surface of the metallic pigment having the amorphous silicon oxide film layer formed thereon by a method in which an alkoxide of, for example, a metal containing at least one selected from Sn, Pd, Pt, and Au as a metal species capable of forming an active site for depositing the metallic particles in the subsequent metallic particle formation step is hydrolyzed and deposited by a sol-gel method, a method in which an alkali is added to a metal salt solution containing the above-mentioned metal to neutralize the solution and deposit the metal layer, or the like.

On the other hand, the step of forming the metal oxide layer on the surface of the metallic pigment that is covered with the amorphous silicon oxide film layer (metal oxide layer formation step) can also be carried out as a preceding step of the metallic particle formation step as mentioned below. That is, the metal oxide layer is formed on the surface of the metallic pigment having the amorphous silicon oxide film layer formed thereon by a method in which an alkoxide of, for example, at least one metal selected from the group consisting of Mg, Sn, Zn, Co, Ni, Fe, Zr, Ti, and Ce as a metal species capable of forming an active site for depositing the metallic particles in the subsequent metallic particle formation step is hydrolyzed and deposited by a sol-gel method, a method in which an alkali is added to a metal salt solution containing the above-mentioned metal to neutralize the solution and deposit the metal oxide layer, a method in which the metallic pigment is brought into contact with an organic metal compound solution containing the above-mentioned metal, or the like. The detail about this step is as mentioned in the section describing about the metal oxide layer. The metal oxide layer formed in this manner preferably contains an oxide of at least one element selected from the group consisting of Mg, Sn, Zn, Co, Ni, Fe, Zr, Ti, and Ce.

When the metal layer formation step and the metal oxide layer formation step are used together, either of the metal layer formation step and the metal oxide layer formation step may be performed first.

Subsequently, the metallic particles are formed in the form of uniform nano-particulate material on the surface of the metallic-particle-supporting layer (i.e., the metal layer or the metal oxide layer) formed as mentioned above, by an electroless plating method or the like (metallic particle formation step). The electroless plating can be carried out by, for example, a method in which the metallic pigment having the metallic-particle-supporting layer formed thereon is transformed into a slurry using water as a dispersion medium and then an electroless plating solution is added to the slurry to cause the reaction. Typically, the electroless plating solution contains at least a metal source from which the metallic particles are mainly formed, a reducing agent, and a complexing agent.

As for the metal source, a water-soluble metal salt containing any one of Al, Ti, Cr, Fe, Co, Ni, Cu, Zn, Ru, Rh, Pd, Ag, Sn, Pt or Au can be used. As for the water-soluble salt, a nitric acid salt, a nitrous acid salt, a sulfuric acid salt, an oxalic acid salt, a carbonic acid salt, a chloride, an acetic acid salt, a lactic acid salt, a sulfamic acid salt, a fluoride, an iodide, a cyanide or the like can be used.

As for the reducing agent, hypophosphorous acid, formaldehyde, boron hydride, dimethylamine borane, trimethylamine borane, hydrazine, glucose, tartaric acid, an alkali metal salt of any one of these compounds, or the like can be used.

As for the complexing agent, a carboxylic acid such as succinic acid, an oxycarboxylic acid such as citric acid and tartaric acid, an organic acid such as glycine, EDTA and aminoacetic acid, an alkali metal salt or an ammonium salt of any one of these acids, or the like can be used. When the complexing agent is used, the metallic particles can be formed in a stable manner.

By employing the above-mentioned method, it becomes possible to allow the metallic particles to be uniformly deposited on the metallic-particle-supporting layer (i.e., the metal layer or the metal oxide layer) with a predetermined spacing as mentioned above (i.e., to form the metallic particles to directly cover a part of the metallic-particle-supporting layer (the metal layer or the metal oxide layer)).

Prior to the metallic particle formation step, the metallic-particle-supporting layer (i.e., the metal layer or the metal oxide layer) may be subjected to a surface activating treatment with a solution containing Sn, Pt, Pd, Au or the like as a pre-treatment.

In the present invention, it is preferred that an anti-corrosion layer including a single film of at least one of an organic compound or a surfactant or a mixture film containing a mixture of the organic compound or the surfactant is formed on the metallic particles. When the anti-corrosion layer contains aluminum and/or silicon, the anti-corrosion layer can be formed by adding a compound containing aluminum and/or silicon to a slurry-like or past-like suspension that is prepared by suspending the metallic pigment having at least the amorphous silicon oxide film layer and the metallic particles formed thereon in a hydrophilic solvent and then stirring or kneading the resultant mixture, thereby adhering the compound containing aluminum and/or silicon onto the surface of the metallic pigment.

In the present invention, it is preferred that a step of forming a weather-resistant coating layer (weather-resistant coating layer formation step) is included subsequent to the metallic particle formation step. When the weather-resistant coating layer contains aluminum and/or silicon, the metallic pigment having at least the metallic particles formed thereon as mentioned above and a solution containing aluminum and/or silicon are stirred or kneaded while keeping the state of a slurry or a paste to form a hydration film and the hydration film is then heated, thereby forming a weather-resistant coating layer including a single film of at least one of an oxide, a hydroxide and a hydrate of aluminum and/or silicon, or a mixture film containing a mixture of the oxide, the hydroxide or the hydrate. When the weather-resistant coating layer contains cerium, the metallic pigment having at least the metallic particles formed thereon are added to a solution in which cerium acetate, cerium nitrate, a cerium alkoxide, a cerium sol or the like is dissolved or dispersed and the resultant mixture is then stirred or kneaded while being heated and while keeping a basic atmosphere, thereby forming a weather-resistant coating layer including a single film of at least one of an oxide, a hydroxide and a hydrate of cerium, or a mixture film containing a mixture of the oxide, the hydroxide or the hydrate.

When the above-mentioned weather-resistant coating layer is formed, it is preferred that a coupling treatment step is employed in combination. For example, when the weather-resistant coating layer contains aluminum and/or silicon, the coupling treatment is carried out by a method in which the metallic pigment on which the metallic particles have been formed and a solution containing aluminum and/or silicon are stirred or kneaded together in a state of a slurry or a paste and then a coupling agent is added to the resultant product, or the like. When the weather-resistant coating layer contains cerium, the coupling treatment is carried out by a method in which the metallic pigment on which the metallic particles have been formed is added to a solution or dispersion of a cerium compound, the resultant mixture is stirred or kneaded while being heated and while keeping a basic atmosphere, and a coupling agent is then added to the stirred or kneaded product, or the like. Alternatively, a method in which the metallic pigment on which the weather-resistant coating layer has been formed is dispersed in a solvent such as isopropyl alcohol to form a slurry and a coupling agent is then added to the slurry, or the like may be employed.

In the present invention, subsequent to the metallic particle formation step, a step of forming a resin covering layer (also serving as the weather-resistant coating layer) (resin covering layer formation step) may also be included. In the step of forming the resin covering layer, the metallic pigment on which at least the metallic particles have been formed is dispersed in a non-polar solvent such as mineral spirit, heptane, octane and isoparafin, the above-mentioned monomer is added to the resultant dispersion, and a polymerization initiator such as benzoyl peroxide, lauroyl peroxide and azobisisobutyronitrile is then added to the resultant mixture under an inert atmosphere at 50 to 150° C., more preferably 70 to 100° C., while mixing by stirring. Subsequently, the stirring is continued until the monomer is fully polymerized (for 1 to 20 hours, more preferably 3 to 10 hours), the resultant slurry is subjected to a solid-liquid separation procedure after the completion of the reaction to produce a past-like composition. In this manner, the resin covering layer can be formed.

The colored metallic pigment according to the present invention can be prepared by the above-mentioned method.

Further, the colored metallic pigment thus prepared may be mixed with a coating resin and, if necessary, other colored pigment, other extender pigment, other dye, other additive and so on by a conventional known method, thereby preparing the resin composition according to the present invention. Furthermore, a cosmetic containing the colored metallic pigment according to the present invention can be prepared by a conventional known method.

EXAMPLES

The present invention is described below in more detail with reference to specific examples: however, the present invention is not limited to these examples.

Example 1

To 3 g of aqueous hydrogen peroxide containing 30 mass % of hydrogen peroxide was added 0.3 g of a metal molybdenum powder in portions, thereby causing the reaction between these components. The resultant solution was dissolved in 500 g of isopropyl alcohol (hereinafter, abbreviated as "IPA"), and thereto was further added 40 g (i.e., 30 g in terms of aluminum content) of a commercially available aluminum pigment (flaky aluminum, trademark: "5422NS" (produced by Toyo Aluminium K. K.), solid content: 75 mass %, average particle size: 19 μm, average thickness: 1 μm)) as a metallic pigment. The resultant was stirred and mixed at 75° C. for 1 hour, thereby obtaining a slurry. In this manner, a metallic pigment having molybdenum oxide formed on the surface thereof as an under layer was obtained.

Subsequently, aqueous ammonia and 80 g of water were added to the above slurry to adjust the pH value of the slurry to 10.0. To the pH-adjusted slurry (i.e., solvent mainly containing a hydrophilic solvent in which the metallic pigment having the under layer formed thereon was dispersed) was gradually added 12 g of tetraethoxysilane as an organosilicon compound and 12 g of IPA.

Thereafter, while keeping the temperature at 75° C., 172 g of tetraethoxysilane and 172 g of IPA were further added gradually, and 3 g of N-2-(aminoethyl)-3-aminopropylmethyldimethoxysilane and 100 g of IPA were simultaneously added gradually, and the resultant was stirred and mixed for a total of 6 hours since the start of the first addition of tetraethoxysilane to hydrolyze the organosilicon compound, thereby allowing an amorphous silicon oxide film to be deposited on (the under layer of) the metallic pigment. Subsequently, the slurry was subjected to a solid-liquid separation procedure using a filter, thereby forming an amorphous silicon oxide film layer on the surface of the metallic pigment (amorphous silicon oxide film layer formation step). Hereinafter, the metallic pigment in this state was termed "silica-coated aluminum pigment".

Then, 10 g of the silica-coated aluminum pigment obtained in the above-mentioned step was dispersed in 300 g of an aqueous solution containing 40 g of tin chloride and 2 g of hydrochloric acid with stirring, and then a 10% aqueous sodium hydroxide solution was dropwise added thereto in portions until the pH value of the solution reached 7.0 while keeping the slurry temperature at 30° C. After the completion of the dropwise addition, the stirring was continued for 1 hour. The resultant slurry was again subjected to a solid-liquid separation procedure and washed with water to allow a tin oxide layer to be deposited on the surface of the silica-coated aluminum pigment, thereby forming the tin oxide layer as a metallic-particle-supporting layer (metal oxide layer) (metallic-particle-supporting layer (metal oxide layer) formation step). Hereinafter, the metallic pigment in this state was termed "metallic-particle-supporting-layer-covered aluminum pigment".

Subsequently, 10 g of the metallic-particle-supporting-layer-covered aluminum pigment obtained in the above-mentioned step was dispersed in 800 g of an electroless silver plating solution containing 3 g of silver nitrate, 2 g of formaldehyde and 10 g of aqueous ammonia, and the resultant was held at 30° C. for 1 hour. In this manner, metallic particles (silver particles) were formed on the surface of the metallic-particle-supporting layer by an electroless plating method (metallic particle formation step). Hereinafter, the metallic pigment in this state was termed "metallic-particle-adhered aluminum pigment". The metallic-particle-adhered aluminum pigment had such a form that the metallic particles were uniformly formed with a regular spacing on the metallic-particle-supporting layer (i.e., the metallic particles were formed to directly cover a part of the metallic-particle-supporting layer).

The thus-obtained metallic-particle-adhered aluminum pigment was subjected to a solid-liquid separation procedure and then dried, thereby obtaining a colored aluminum pigment that was the colored metallic pigment according to the present invention. The colored aluminum pigment was visually observed, and it was found that the colored aluminum pigment had an interference color that changed from a pink color to a green color depending on the viewing angle and had a good metallic feeling.

Cross sections of 50 pieces of the thus-obtained colored aluminum pigment were observed with a scanning electron microscope, and it was found that the amorphous silicon oxide film layer had an average thickness of 627 nm. The colored aluminum pigment was also observed with a transmission electron microscope, and it was found that the metallic-particle-supporting layer (metal oxide layer) had a thickness of 2 nm, and the metallic particles had an average particle size of 5 nm and were uniformly formed with a spacing of 0.5 nm on the metallic-particle-supporting layer (metal oxide layer).

Comparative Example 1

The same procedure as in Example 1 in Japanese Patent Laying-Open No. 2012-031232 (PTD 2) was carried out, thereby producing a colored metallic pigment.

To 3 g of aqueous hydrogen peroxide containing 30 mass % of hydrogen peroxide was added 0.3 g of a metal molybdenum powder in portions, thereby causing the reaction between these components. The resultant solution was dissolved in 500 g of isopropyl alcohol (hereinafter, abbreviated as "IPA"), and thereto was further added 40 g (i.e., 30 g in terms of aluminum content) of a commercially available aluminum pigment (flaky aluminum, trademark: "5422NS" produced by Toyo Aluminium K. K., a solid content: 75 mass %, average particle size: 19 μm, average thickness: 1 μm) as a metallic pigment. The resultant was stirred and mixed at 75° C. for 1 hour, thereby obtaining a slurry. In this manner, a metallic pigment having molybdenum oxide formed on the surface thereof as an under layer was obtained.

Subsequently, aqueous ammonia and 80 g of water were added to the above slurry to adjust the pH value of the slurry to 10.0. To the pH-adjusted slurry (i.e., solvent mainly containing a hydrophilic solvent in which the metallic pigment having the under layer formed thereon was dispersed) was gradually dropwise added a solution prepared by dissolving 40 g of tetraethoxysilane as an organosilicon compound in 40 g of IPA, and the resultant was further stirred and mixed at 75° C. for 2 hours to hydrolyze the organosilicon compound, thereby allowing amorphous silicon oxide to be deposited on the metallic pigment (under layer). Subsequently, the slurry was subjected to a solid-liquid separation procedure using a filter, thereby forming an amorphous silicon oxide film layer on the surface of the metallic pigment (amorphous silicon oxide film layer formation step). Hereinafter, the metallic pigment in this state was termed "silica-coated aluminum pigment".

Then, 10 g of the silica-coated aluminum pigment obtained in the above-mentioned step was dispersed in 300 g of an aqueous solution containing 40 g of tin chloride and 2 g of hydrochloric acid with stirring, and then a 10% aqueous sodium hydroxide solution was dropwise added thereto in portions until the pH value of the solution reached 7.0 while keeping the slurry temperature at 30° C. After the completion of the dropwise addition, the stirring was continued for 1 hour. The resultant slurry was again subjected to a solid-liquid separation procedure and washed with water to allow a tin oxide layer to be deposited on the surface of the silica-coated aluminum pigment, thereby forming the tin oxide layer as a metal oxide layer (metal oxide layer formation step). Hereinafter, the metallic pigment in this state was termed "metal-oxide-layer-covered aluminum pigment".

Subsequently, 10 g of the metal-oxide-layer-covered aluminum pigment obtained in the above-mentioned step was dispersed in 800 g of an electroless silver plating solution containing 3 g of silver nitrate, 2 g of formaldehyde and 10 g of aqueous ammonia, and the resultant was held at 30° C. for 1 hour. In this manner, metallic particles (silver particles) were formed on the surface of the metal oxide layer by an electroless plating method (metallic particle formation step). Hereinafter, the metallic pigment in this state was termed "metallic-particle-adhered aluminum pigment". The metallic-particle-adhered aluminum pigment had such a form that the metallic particles were uniformly formed with a regular spacing on the metal oxide layer (i.e., the metallic particles were formed to directly cover a part of the metal oxide layer).

The thus-obtained metallic-particle-adhered aluminum pigment was subjected to a solid-liquid separation procedure and then dried, thereby obtaining a colored aluminum pigment having a blue color. The colored aluminum pigment was visually observed, and it was found that the colored aluminum pigment had an interference color that changed from a bluish-purple color to a dark brown color depending on the viewing angle and had a good metallic feeling.

Cross sections of 50 pieces of the thus-obtained colored aluminum pigment were observed with a scanning electron microscope, and it was found that the amorphous silicon oxide film layer had an average thickness of 70 nm. The colored aluminum pigment was also observed with a transmission electron microscope, and it was found that the metal oxide layer had a thickness of 2 nm, and the metallic particles had an average particle size of 5 nm and were uniformly formed with a spacing of 0.5 nm on the metal oxide layer.

<Color Tone Evaluation>

A paint for color measurement was prepared by mixing 5 g of the colored aluminum pigment obtained in Example 1 in the form of a powder and 45 g of nitrocellulose lacquer (trademark: "NC Clear TY" produced by Saito Paint Co., Ltd.) using a stirrer (device name: "MAZERUSTAR" produced by Kurabo Industries, Ltd.). The paint was drawn down on art paper using a 9-mil doctor blade to produce coating paper for color measurement. For the colored aluminum pigment obtained in Comparative Example 1, coating paper for color measurement was also produced in the same way.

After each coating paper dried, color measurement was performed on each coating paper using a variable angle color measurement system (trademark: "GCMS-4 type") and a variable angle spectrophotometer system (trademark: "GSP-2 type") (both produced by Murakami Color Research Laboratory).

As for the color measurement, a* values and b* values in the L*a*b* color system in the case where the incident angle was 45° and the light receiving angle was 40°, 50°, 60°, 70°, and 80° were measured. Table 1 shows the results.

TABLE 1

| | Light receiving angle | a* | b* |
|---|---|---|---|
| Example 1 | 40° | 30.09 | 11.56 |
| | 50° | 0.65 | 30.18 |
| | 60° | −23.56 | 39.48 |
| | 70° | −34.31 | 34.68 |
| | 80° | −31.93 | 24.28 |
| Comparative Example 1 | 40° | 42.58 | −79.55 |
| | 50° | 38.06 | −67.35 |
| | 60° | 44.15 | −71.17 |
| | 70° | 38.81 | −60.01 |
| | 80° | 28 | −44.39 |

As apparent from Table 1, comparison of the results of Example 1 and Comparative Example 1 shows that the change between the a* value in the case where the light receiving angle was 40° and the a* value in the case where the light receiving angle was 80° is significantly greater in Example 1 than that in Comparative Example 1. Therefore, it can be seen that a change in color tone depending on the viewing angle is greater in Example 1. This is assumed to be due to the fact that the amorphous silicon oxide film layer in Example 1 has a thickness of more than 500 nm.

Embodiments and examples of the present invention are described above. However, proper combinations of the constitutions of the respective embodiments and the respective examples are also originally intended.

It should be understood that the embodiments and examples disclosed herein are illustrative and non-restrictive in every respect. The scope of the present invention is defined by the scope of the claims, rather than the description above, and is intended to include any modifications within the scope and meaning equivalent to the scope of the claims.

The invention claimed is:

1. A colored metallic pigment comprising at least:
a metallic pigment;
an amorphous silicon oxide film layer formed on a surface of the metallic pigment;
a metallic-particle-supporting layer formed on a surface of the amorphous silicon oxide film layer; and
metallic particles formed on a surface of the metallic-particle-supporting layer,
the metallic-particle-supporting layer being formed of one or both of a metal layer and a metal oxide layer composed of a metal oxide other than silicon oxide, the metallic-particle-supporting layer having a thickness of less than or equal to 10 nm,
the metallic particles being formed to directly cover a part of the surface of the metallic-particle-supporting layer, the amorphous silicon oxide film layer having a thickness of more than 500 nm.

2. The colored metallic pigment according to claim 1, wherein the amorphous silicon oxide film layer has a thickness within a range of more than 500 nm and less than or equal to 1000 nm, and the metallic particles have an average particle size of less than or equal to 50 nm.

3. The colored metallic pigment according to claim 1, wherein the metal layer contains at least one selected from the group consisting of Sn, Pd, Pt, and Au, and the metal oxide layer contains an oxide of at least one element selected from the group consisting of Mg, Sn, Zn, Co, Ni, Fe, Zr, Ti, and Ce.

4. The colored metallic pigment according to claim 1, wherein the metallic particles contain at least one element selected from the group consisting of Cu, Ni, and Ag.

5. A resin composition containing at least a colored metallic pigment as recited in claim 1.

6. An applied object having a resin composition as recited in claim 5 applied on a base body.

7. A cosmetic containing at least a colored metallic pigment as recited in claim 1.

* * * * *